United States Patent [19]

Calas et al.

[11] Patent Number: 5,175,254

[45] Date of Patent: Dec. 29, 1992

[54] SOLID PHASE PEPTIDE SYNTHESIS USING A POLYACRYLIC SUPPORT IN AQUEOUS SOLUTION

[75] Inventors: Bernard Calas, Montpellier; Jean Mery, Saint Gely Du Fesc; Hanitra Naharisoa, Montpellier; Michel Follet, Aramon, all of France

[73] Assignee: Societe d'Expansion Scientifque Expansia, France

[21] Appl. No.: 766,899

[22] Filed: Sep. 26, 1991

Related U.S. Application Data

[63] Continuation of Ser. No. 412,171, Sep. 25, 1989, abandoned.

[30] Foreign Application Priority Data

Sep. 24, 1988 [GB] United Kingdom ............... 8822502

[51] Int. Cl.⁵ .................... A61K 37/02; C07K 5/00
[52] U.S. Cl. .................................. 530/334; 530/333
[58] Field of Search ............... 525/327.1, 326.7; 530/333, 334

[56] References Cited

U.S. PATENT DOCUMENTS

4,436,874 3/1984 Aspisi et al. ................ 525/327.1

OTHER PUBLICATIONS

Calas et al. "Solid Phase Syntheses Using a New Polyacrylic Resin", 41 Tetrahedron No. 22 pp. 5331-5339 (1985).
Atherton et al. "Peptide Syntheses . . . " J. Chem. Soc. Perkin Transaction I, 538-545 (1981).
Arshady et al. "Peptide Syntheses . . . " J. Chem. Soc. Perkin Trans I, 529-537 (1981).

*Primary Examiner*—Merrell C. Cashion, Jr.
*Assistant Examiner*—B. Celsa
*Attorney, Agent, or Firm*—Lucas & Just

[57] ABSTRACT

This invention relates to solid phase peptide synthesis.

Solid phase peptide synthesis is accomplished on polyacrylic resins (such as those described in EP 0 079 812 and EP 0 081 408 which correspond to U.S. Pat. Nos. 4,436,874 and 4,439,545 respectively) by a method which includes in the coupling protocol steps of washing the resin in water and/or aqueous solution(s).

5 Claims, No Drawings

SOLID PHASE PEPTIDE SYNTHESIS USING A POLYACRYLIC SUPPORT IN AQUEOUS SOLUTION

This is a continuation of application Ser. No. 412,171, filed Sep. 25, 1989, now abandoned.

The present invention relates to solid phase peptide synthesis.

The abbreviations used in this specification are in accordance with the 1983 Recommendations of the IUPAC-IUB Joint Commission on Biochemical Nomenclature, as set out in Eur. J. Biochem, 138, 9-37 (1984). In addition, the following are used:

TFA—trifluoroacetic acid
DCM—dichloromethane
DMF—dimethylformamide
NMP—N-methylpyrrolidine
DMAc—dimethylacetamide Amino acids and their residues are of L-configuration unless otherwise specified, e.g. Ala=L-alanine, DAla=D-alanine. The term (meth)acrylic is used to indicate either acrylic or methacrylic.

The usual methods of solid phase peptide synthesis comprise the following sequence of operations:

1. Deprotection of the Boc group;
2. Washings;
3. Neutralization of $NH_2$ in $\alpha$ position;
4. Washings;
5. Couplings and
6. Washings.

Deprotection and neutralization steps are achieved by treating the resin-peptide with TFA and diisopropylethylamine solutions in DCM. This same solvent is also used for intermediate washings. Whatever the coupling agent used (symmetrical anhydride, dicyclohexylcarbodiimide, hydroxybenzotriazol, etc.), the coupling reaction is conducted either in DCM or in DMF.

Consequently, solid phase peptide synthesis involves large quantities of rather expensive solvents and reagents such as TFA; thus, the cost of a peptide directly depends on the costs of DCM, NMP, DMF, DMAc and TFA used in the synthesis.

Therefore, it would be particularly interesting to find cheaper solvents and reagents in order to lower significantly the manufacturing cost of peptides.

Our European Patent No. 0 079 842 which corresponds to U.S. Pat. No. 4,436,874 describes polyacrylic resins which are copolymers of three monomers as follows:

(i) a first monomer which provides a matrix for the copolymer and is one of
1-(meth)acryloyl-pyrrolidine,
1-(meth)acryloyl-piperidine,
1-(meth)acryloyl-perhydroazepine,
1-(meth)acryloyl-4-methyl-piperazine,
4-(meth)acryloyl-morpholine,
N,N-dimethyl-(meth)acrylamide and
N,N-diethyl-(meth)acrylamide (ii) a second monomer which crosslinks the copolymer and is one of
N,N'-di(meth)acryloyl-diaminomethane and
N,N'-di(meth)acryloyl-1,2-diaminoethane, and (iii) a third monomer which activates the copolymer and is one of the following acids
2-(meth)acrylamido-acetic acid,
3-(meth)acrylamido-propionic acid,
4-(meth)acrylamido-butyric acid,
6-(meth)acrylamido-hexanoic acid,
N-(meth)acryloyl-L-alanine,
N-(meth)acryloyl-L-valine,
N-(meth)acryloyl-L-leucine,
N-(meth)acryloyl-L-phenylalanine,
N-(meth)acryloyl-L-tyrosine,
N-(meth)acryloyl-L-methionine,
N-(meth)acryloyl-L-lysine, and
N-(meth)acryloyl-L-proline
or is a methyl ester of one of those acids.

These copolymers have free carboxy or methoxycarbonyl groups deriving from the third monomer. Our European Patent No. 81408 which corresponds to U.S. Pat. No. 4,439,545 describes further polyacrylic resins in which these groups are amidified with ethylene diamine. It also describes the use of these further polyacrylic resins in solid phase peptide synthesis, but only in conjunction with the expensive solvents conventionally used with polystyrene resins, as discussed hereinabove.

The invention provides a method for solid phase peptide synthesis, the method comprising attaching a first amino acid residue to a polyacrylic resin, coupling one or more further amino acid residues to form the desired peptide and detaching the peptide from the resin, characterised in that the coupling protocol includes steps of washing the resin in water and/or aqueous solution(s).

The method of the invention takes advantage of the hydrophilic properties possessed by polyacrylic resins unlike polystyrene resins. The polyacrylic resins for use in the method of the invention are preferably those described in our European Patents Nos. 0 079 842 and 0 081 408 as above discussed.

The first amino acid residue may be fixed on the matrix through the glycolamide moiety (B. Calas and Al., Tetrahedron, 1985, 41, 5331). Previous attempts with other labile binders such as

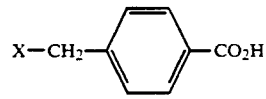

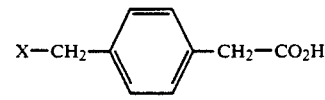

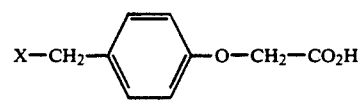

wherein X=Br, Cl or OH proved unsatisfactory.

The resin may then be washed in water. The next amino acid of the peptide sequence to be built may be added according to the following protocol (applicable when the protecting group is Boc):

1. Washing: distilled water—2 to 4 times, 2 mn each (as used herein, the abbreviation "mn" stands for minutes);
2. Deprotection: HCl (6N) in water—once, 2 mn and once again, 30 minutes;
3. Washing: distilled water—4 to 6 times, 2 mn each;
4. Neutralization: 1 equivalent of borate buffer 12.5 mM pH 8.5–9.0—once, 1 to 2 mn and once again, 1 to 2 mn;

5. Washing: distilled water—4 to 6 times, 1 to 2 mn each;
6. Washing: DMF—twice, 1 to 2 mn each;
7. Coupling: symmetrical anhydride (2 equivalents, twice in DMF)
8. Washing: DMF or NMP—twice, 2 mn each; and
9. Washing: distilled water—4 times, 2 mn each.

The progress of the coupling reaction may be controlled by ninhydrine or fluorescamine.

Alternatively, when the protecting group is Fmoc, the elongation protocol may be as follows:
1. Washing: distilled water—4 to 6 times, 2 mn each;
2. Deprotection: piperidine or diethylamine in water;
3. Washing: isopropanol, twice, 2 mn each; distilled water—4 to 6 times, 2 mn each;
4. Optionally washing: DMF—once, 2 mn;
5. Coupling: symmetric anhydride (3 times in excess in DMF) and
6. Washing: DMF (twice, 2 mn each); distilled water—6 times, 2 mn each.

When the synthesis is complete, the peptide is separated from the matrix by a selective breaking of the glycolamide bond obtained by one of the following treatments:
NaOH in isopropanol,
$NH_3$ in trifluoroethanol or methanol or ethanol or isopropanol,
$N_2H_4$ in DMF and
$CH_3OH$ in triethylamine.

With this method, the reference peptide of Dorman (Leu Ala Gly Val) and LHRH analogs were obtained with yields of approx. over 50%.

The invention will be better understood from the description of the following examples:

EXAMPLE 1

Synthesis of DTrp[6]-LHRH:
pyro-Glu-His-Trp-Ser-Tyr-DTrp-Leu-Arg-Pro-Gly 5 g of a polyacrylic resin (0.55 mmol $NH_2$/g), prepared by copolymerizing 1-acryloyl-pyrrolidine, N,N'-diacryloyl-1,2-diaminoethane and methyl 2-acrylamidoacetate as described in example 19 of Ep 0 079 842, were treated as follows:
1/ washes with DCM (4 times, 2 mn each)
2/ neutralization with 5% diisopropylethylamine in DCM (2 times, 2 mn each)
3/ washes with DCM (4 times, 2 mn each).

4.29 g (0.0165 mol) of bromoacetic anhydride in 50 ml of DCM were added to the resin. After 45 mn of shaking, the DCM solution was removed by filtration and the brominated support was washed as follows:
1/ DCM (4 times, 2 mn each)
2/ DMF (4 times, 2 mn each)

Cesium salt of BocGlyOH (4.22 g, 0.0137 mol) prepared according to Mery et al. (Int. J. Protein Peptide Res. 1988, 31, 412) was dissolved in DMF (75 ml), and this solution was added to the resin. The mixture was shaken for two days at ambient temperature. At this time, DMF was drained and the polymer washed with:
1/ DMF (10 times, 2 mn each)
2/ Methanol (4 times, 2 mn each)
3/ DCM (4 times, 2 mn each)
4/ Diethylether (4 times, 2 mn each)

The resin was dried under high vacuum in presence of KOH pellets for 12 hours. The amount of Gly linked was 0.483 mmol/g, determined by amino acid analysis after hydrolysis in 6N HCl in evacuated and sealed tubes at 110° C. for 24 hours.

BocGly-Resin (4.47 g) was washed with water (4 times, 2 mn each) and the Boc group was cleaved using 6N HCl in water (2 times, once 2 mn and once again 30 mn). HCl was removed by filtration and the resin washed with water (6 times, 2 mn each). The neutralization was performed using borate buffer (12.5 mmol, pH 9), the resin being treated twice with 50 ml of buffer (1 mn each). After washing with water (6 times, 2 mn each) and with DMF (2 times, 2 mn each) symmetrical anhydride of BocProOH in DMF (50 ml) was added to the resin.

The solution of symmetrical anhydride was prepared as follows: BocProOH (3.55 g, 0.0165 mol) was dissolved in 40 ml of DMF, the solution was cooled at 0° C. and dicyclohexylcarbodiimide (1.69 g, 8.25 mmol) in 10 ml of DCM was added. After stirring at 0° C. for 30 mn and filtration, the solution was evaporated under high vacuum without heating and the residue dissolved in DMF and added to the resin. The mixture was shaken for 30 mn, at this time the qualitative ninhydrin test of Kaiser et al.(Anal.Biochem. 1970, 34, 575) was negative indicating a coupling yield higher than 99.6%. The DMF was then removed and the support was washed twice with DMF (2 mn each) and with water (4 times, 2 mn each).

This protocol was used to incorporate the other amino acids of the DTrp[6]-LHRH sequence. The symmetrical anhydrides were prepared using: BocArg(Mts)OH (7.52 g, 0.0165 mol), BocLeuOH (4.11 g, 0.0165 mol), BocDTrpOH (5.02 g, 0.0165 mol), BocTyr (2.6 dichlorobenzyl)OH or BocTyr (2.6 DCB)OH (7.26 g, 0.0165 mol), BocSer(Bzl)OH (4.86 g, 0.0165 mol), BocTrpOH (5.02 g, 0.0165 mol), BocHis (Dinitrophenyl)OH or BocHis (Dnp)OH (6.94 g, 0.0165 mol), pyro-GluOH (2.13 g, 0.0165 mol).

After the incorporation of pyro-GluOH, the resin was washed with methanol (4 times, 2 mn each), with diethylether (4 times, 2 mn each) and dried in high vacuum at ambient temperature for 48 hours.

The peptide-resin was then treated with thiophenol (10 ml) in DMF (50 ml) to remove the dinitrophenyl group on the histidine side-chain.

After 45 mn of shaking, the thiophenol solution was drained and the resin washed with DMF (4 times, 2 mn each), DCM (4 times, 2 mn each) and diethylether (4 times, 2 mn each). The resin was dried under high vacuum for 12 hours. It was treated twice (30 mn each) at 0° C. with 50 ml of the following precooled solution trifluoromethansulfonic acid (3.6 ml), anisole (4 ml), thioanisole (4 ml), metacresol (4 ml) and trifluoroacetic acid (40 ml). After the end of deprotection, the resin was washed with DCM (2 times, 2 mn each), DCM/DMF (50-50) (2 times, 2 mn each), diisopropylethylamine 5% in DCM (2 times, 1 mn each), DMF (3 times, 2 mn each), isopropanol-water (70-30) (3 times, 2 mn each). Peptide-resin was then suspended in a $NH_3$ saturated trifluoroethanolic solution (250 ml).

The mixture was shaken at ambient temperature for 15 hours, the trifluoroethanolic solution containing deprotected DTrp[6]-LHRH was collected and the support was washed with water (4 times, 2 mn each), methanol (4 times, 2 mn each) and water (6 times, 2 mn each). The filtrates were pooled, the pH was brought to about 4 with 1N hydrochloric acid they were concentrated under vacuum without heating. The residue was fractionated on a column of carboxymethylcellulose (Wathman CM 52, 10×2 cm) with a linear gradient of NaCl (10 mM AcONa pH 5.0 to 10 mM AcONa, 0.15M NaCl pH 5.0). Appropriate fractions were pooled, lyophilized and desalted by gel filtration on a column (100×2.5 cm) of Sephadex G10 in 10M HCl. The peptide fraction was then purified by HPLC on a column (270×20 mm) of Lichrosorb RP18 (10 μm) using trifluoroacetic acid (TFA) 0.01% in water and acetonitrile as eluents.

Yield: 51% (based on the starting amino groups of the support).

Amino acid analysis: Glu 0.99 (1), Leu 1.0 (1), His 1.0 (1), Trp 1.89 (2), Ser 0.96 (1), Tyr 0.97 (1), Pro 0.99 (1), Gly 1.07 (1).

For some amino acids which are less stable in acidic conditions, analytical values may be lower than the expected ones due to degradation of the same.

The same method was used for the following peptides:

Dorman peptide: Leu Ala Gly ValOH
yield=46.6%
Gly=0.96, Ala=0.94, Val=1.05, Leu=1.04
Laminine: Tyr Ile Gly Ser ArgNH$_2$
yield=35.6%
Ser=0.75, Gly=1.03, Ile=0.99, Tyr=1, Arg=0.99.
CDC 28 kinose protein from the cellular cycle of "Pombee" yeast
yield=44.1% (crude peptide)
Tyr Lys Ala Leu Asp Leu Arg Pro GlyOH
Asp=1, Gly=1.08, Ala=1, Leu=1.05×2, Tyr=0.99,
Arg=0.99, Lys=1, Pro=1.
Tyrosine phosphatase
yield=58.6% (crude peptide)
Cys Ser Asp Ser Glu Lys Leu Asn Leu Asp Ser IleOH
Asp=0.95×3, Ser=0.58×3, Glu=0.67, Ile=1.1, Leu=1.1.
Oncogene: Phe Arg Gly Thr Leu Arg
yield=53.4%
Phe=0.97, Arg=2×1.1, Gly=1.02, Thr=0.99, Leu=1.

EXAMPLE 2

Synthesis of Leu-Ala-Gly-Val 1 g of the polyacrylic resin used in example 1 was treated as follows:

1/ washes with DCM (4 times, 2 mn each)
2/ neutralization with 5% diisopropylethylamine in DCM (2 times, 2 mn each)
3/ washes with DCM (4 times, 2 mn each)

0.858 g (3.3 mmol) of bromoacetic anhydride in 10 ml of DCM was added to the resin. After 45 mn of shaking, the DCM solution was removed by filtration and the brominated support was washed as follows:

1/ DCM (4 times, 2 mn each)
2/ DMF (4 times, 2 mn each)

Cesium salt of FmocValOH (1.29 g, 2.75 mmol) prepared according to Mery et al. (Int. J. Peptide Protein Res.1988, 31, 412), was dissolved in DMF (15 ml) and the solution was added to the resin. The suspension was shaken at ambient temperature for three days. At this time, the DMF was drained and the polymer was washed with:

1/ DMF (10 times, 2 mn each)
2/ Methanol (4 times, 2 mn each)
3/ DCM (4 times, 2 mn each)
4/ Diethylether (4 times, 2 mn each)

The resin was dried under high vacuum, in presence of KOH pellets for 12 hours. The amount of Val linked was 0.492 mmol/g, determined by amino acid analysis, after hydrolysis in 6N HCl in evacuated and sealed tubes for 24 hours.

FmocVal-Resin (1.1 g) was washed with water (4 times, 2 mn each) and the Fmoc group was cleaved using 10% piperidine or diethylamine in water (2 times, 2 mn each). The resin was then washed with isopropanol (2 times, 2 mn each) and with water (4 times, 2 mn each).

Symmetrical anhydride of FmocGlyOH in DMF (15 ml) was added to the support. The solution of symmetrical anhydride was prepared as follows:

FmocGlyOH (0.981 g, 3.3 mmol) was dissolved in DCM (15 ml), the solution was cooled to 0° C. and dicyclohexylcarbodiimide (0.339 g, 1.65 mmol) in DCM (10 ml). The cloudy mixture was stirred for 20 mn at 0° C., the precipitate of dicyclohexylurea was removed by filtration and the filtrate was concentrated under vacuum at room temperature. The oily residue was dissolved in DMF (15 ml) and the solution was added to the resin. The mixture was shaken at room temperature for 45 mn, at this time the qualitative ninhydrin test of Kaiser et al. (Anal. Biochem. 1970, 34, 575) was negative. The DMF was removed by filtration and the support was washed with DMF (2 times, 2 mn each) and then with water (6 times, 2 mn each).

This protocol was used to incorporate the following amino acids: Leu and Ala. The symmetrical anhydride were prepared starting from 1.16 g (3.3 mmol) of FmocLeuOH and 1.02 g (3.3 mmol) of FmocAlaOH. After the completion of the synthesis the peptide-resin adduct was washed with isopropanol (4 times, 2 mn each), water (4 times, 2 mn each) and isopropanol-water (70-30) (4 times, 2 mn each).

Peptide-resin was then suspended in isopropanol-water (70-30) and 1.1 ml of 1N NaOH were added. The mixture was shaken at ambient temperature for 5 hours, the isopropanol-water solution containing the Leu-Ala-Gly-Val was collected and the support washed with water (4 times, 2 mn each), methanol (4 times, 2 mn each) and water (4 times, 2 mn each). The filtrates were pooled, the pH was brought to 4 with 1N HCl, the solution was concentrated under vacuum at room temperature. The residue was purified by HPLC on a column (250×20 mm) of Lichrosorb RP 18 (10 μm) using TFA 0.1% in water and acetonitrile as eluants.

Yield: 54% (based on the starting amino groups of the support).

Amino acid analysis: Leu 1.02 (1), Ala 0.99 (1), Gly 1.1 (1), Val 1.0 (1).

The same method was used for the synthesis of the following peptides:

Dorman peptide: Leu Ala Gly ValOH
yield=46.6%
Gly=0.93, Ala=0.91, Val=1.01, Leu=1.
Laminine: Tyr Ile Gly Ser ArgNH$_2$
yield=46.3%
Ser=0.79, Gly=1.01, Ile=0.96, Tyr=0.89, Arg=0.93.
CDC 28 kinase protein from the cellular cycle of "Pombee" yeast
yield=48.6% (crude peptide)
Tyr Lys Ala Leu Asp Leu Arg Pro GlyOH
Asp=0.97, Gly=1.02, Ala=0.98, Leu=1.02×2, Tyr=0.98, Arg=0.96, Lys=1, Pro=0.97.

Tyrosine phosphatase
yield = 61.6% (crude peptide)
Cys Ser Asp Ser Glu Lys Leu Asn Leu Asp Ser IleOH Asp = 0.99 × 3, Ser = 0.63 × 3, Glu = 0.73, Ile = 1.03, Leu = 1.

Oncogene: Phe Arg Gly Thr Leu Arg
yield = 49.2%

Phe = 1, Arg = 2 × 1.04, Gly = 1, Thr = 0.96, Leu = 0.98.

We claim:

1. A method for solid phase peptide synthesis, the method comprising attaching a first amino acid residue selected from the twenty naturally occurring L-alpha amino acids to a hydrophilic polyacrylic resin, coupling one or more further amino acid residues of the twenty naturally occurring L-alpha amino acids to form a peptide and detaching the peptide from the resin, characterized in that the coupling of the said amino acid residues to the polyacrylic resin includes steps of washing the resin in water, one or more aqueous solutions, or a combination of the foregoing.

2. The method of claim 1 wherein the hydrophilic polyacrylic resin is a copolymer of three monomers as follows:
   (1) a first monomer which provides a matrix for the copolymer and is selected from the group consisting of:
   1-(meth)acryloyl-pyrrolidine,
   1-(meth)acryloyl-piperidine,
   1-(meth)acryoloyl-perhydroazepine,
   1-(meth)acryloyl-4-methyl-piperazine,
   4-(meth)acryloyl-morpholine,
   N,N-dimethyl-(meth)acrylamide and
   N,N-diethyl-(meth)acrylamide
   (ii) a second monomer which crosslinks the copolymer and is selected from the group consisting of:
   N,N'-di(meth)acroyloyl-diaminomethane and
   N,N'-di(meth)acroyloyl 1-1-diaminoethane, and
   (iii) a third monomer which activates the copolymer and is selected from the group consisting of the following acids:
   2-(meth)acrylamido-acetic acid,
   3-(meth)acrylamido-propionic acid,
   4-(meth)acrylamido-butyric acid,
   6-(meth)acrylamido-hexanoic acid
   N-(meth)acryloyl-L-alanine,
   N-(meth)acryloyl-L-valine,
   N-(meth)acryloyl-L-leucine,
   N-(meth)acryloyl-L-phenylalanine,
   N-(meth)acryloyl-L-tyrosine,
   N-(meth)acryloyl-L-methionine,
   N-(meth)acryloyl-L-lysine,
   N-(meth)acryloyl-L-proline
   and methyl esters of each of the acids.

3. The method of claim 2 wherein the hydrophilic polyacrylic resin has been amidified with ethylene diamine.

4. The method of any of claims 1, 2 or 3 wherein the N-protecting group used in the amino acid coupling is Boc and the coupling comprises the following steps:
   1. Washing: distilled water—2 to 4 times 2 mn each;
   2. Deprotection: 6N HCl in water—once, 2 mn and once again, 30 minutes;
   3. Washing: distilled water—4 to 6 times, 2 mn each;
   4. Neutralization: 1 equivalent of borate buffer 12.5 mM pH 8.5-9.0—once, 1 to 2 mn and once again, 1 to 2 mn;
   5. Washing: distilled water—4 to 6 times, 1 to 2 mn each;
   6. Washing: DMF—twice, 1 to 2 mn each;
   7. Coupling: symmetrical anhydride;
   8. Washing: DMF or NMP—twice, 2 mn; each and
   9. Washing: distilled water—4 times, 2 mn each.

5. The method of any of claims 1, 2 or 3 wherein the N-protecting group used in he amino acid coupling is Fmoc and the coupling comprises the following steps:
   1. Washing: distilled water—4 to 6 times, 2 mn each;
   2. Deprotection: piperidine or diethylamine in water;
   3. Washing: isopropanol, twice, 2 mn each; distilled water—4 to 6 times, 2 mn each;
   4. Optionally washing: DMF—once, 2 mn;
   5. Coupling: symmetric anhydride, 3 times in excess in DMF, and
   6. Washing: DMF twice, 2 mn each; distilled water—6 times, 2 mn each.

* * * * *

UNITED STATES PATENT AND TRADEMARK OFFICE
CERTIFICATE OF CORRECTION

PATENT NO. : 5,175,254
DATED : December 29, 1992
INVENTOR(S) : Bernard Calas et al.

It is certified that error appears in the above-identified patent and that said Letters Patent is hereby corrected as shown below:

Column 3, line 44, change "Ep" to --EP--.

Column 4, line 66, after "acid" insert --;--.

Column 7, line 40 (claim 2), change "1-1-diaminoethane" to --1-2-diaminoethane--.

Column 8, line 33 (claim 5), change "he" to --the--.

Signed and Sealed this

Twelfth Day of October, 1993

Attest:

BRUCE LEHMAN

Attesting Officer  Commissioner of Patents and Trademarks